United States Patent [19]

Pitt

[11] 4,007,224
[45] Feb. 8, 1977

[54] PROCESS OF MANUFACTURING DICHLOROACETYL CHLORIDE
[75] Inventor: Harold M. Pitt, Lafayette, Calif.
[73] Assignee: Stauffer Chemical Company, Westport, Conn.
[22] Filed: Mar. 5, 1975
[21] Appl. No.: 553,936

Related U.S. Application Data
[63] Continuation-in-part of Ser. No. 494,671, Aug. 5, 1974, abandoned.
[52] U.S. Cl. .......................................... 260/544 Y
[51] Int. Cl.² ........................................ C07G 51/58
[58] Field of Search .................................. 260/544
[56] References Cited
UNITED STATES PATENTS

| | | | |
|---|---|---|---|
| 1,976,265 | 10/1934 | Mugdom et al. | 260/544 Y |
| 2,292,129 | 8/1942 | Kirkbride | 260/544 Y |
| 3,509,210 | 4/1970 | Gaertner et al. | 260/544 Y |
| 3,630,867 | 12/1971 | Petz | 260/544 Y |

Primary Examiner—Norman Morgenstern
Attorney, Agent, or Firm—Michael J. Bradley

[57] ABSTRACT

An improved process for the production of dichloroacetyl chloride by liquid phase photooxidation of trichloroethylene with oxygen or air in the presence of a catalytic amount of free chlorine or bromine to yield a mixture of dichloroacetyl chloride and trichloroethylene oxide is disclosed herein. The improvement in the process being conducting the reaction in the presence of a catalytic amount of primary or secondary amides, preferably dimethylformamide, which causes the trichloroethylene oxide to rearrange exothermically to dichloroacetyl chloride.

8 Claims, No Drawings

PROCESS OF MANUFACTURING DICHLOROACETYL CHLORIDE

This application is a continuation-in-part of U.S. Ser. No. 494,671, filed Aug. 5, 1974, now abandoned.

BACKGROUND OF THE INVENTION

In the usual practice for manufacturing dichloroacetyl chloride (DCAC) in the liquid phase, trichloroethylene (TCE) is treated with oxygen and/or air in the presence of a catalytic amount of free chlorine and a chlorine activating source such as short wavelength light, usually ultraviolet light with vigorous agitation under pressure. The photo-oxidation of trichloroethylene provides approximately a 50:50 mixture of dichloroacetyl chloride and trichloroethylene oxide (TCEO).

After this reaction is essentially complete, the mixture of dichloroacetyl chloride and trichloroethylene oxide is subjected to an exothermic catalytic rearrangement of the trichloroethylene oxide to dichloroacetyl chloride. This is brought about by adding a secondary or tertiary amine catalyst to the reaction mixture while cooling the same. A secondary or tertiary amine has been described as dimethyl amine, diethyle amine, dibutyl amine, trimethyl amine, triethyl amine, tributyl amine, N-methylaniline, N,N-dimethylaniline, pyridine, piperdine, picolines, quinolines and mixtures of these amines. The prior art described processes indicates that essentially quantitive yields of rearrangement from trichloroethylene oxide to dichloroacetyl chloride are obtained. A more complete description of prior art processes may be found in U.S. Pat. No. 3,630,867.

It has been found in practice, however, that the manufacture of dichloroacetyl chloride by the above-described process has serious drawbacks. First, since the rearrangement reaction of trichloroethylene oxide to dichloroacetyl chloride is both rapid and exothermic, a serious problem of control of the rearrangement reaction results upon addition of the secondary or tertiary amines at or near the end of the oxidation of trichloroethylene. And second, upon addition of the secondary or tertiary amines to the reaction during the course of the reaction, to effect the rearrangement of the trichloroethylene oxide to dichloroacetyl chloride as it is formed, colored by-product chemical species are formed, which as the rearrangement reaction progresses effect the color of thereaction mass, changing it from clear to a light amber to dark brown or purple. The specific color will, of course, depend upon the amount of secondary or tertiary amines being employed as catalyst. As the rearrangement reaction of trichloroethylene oxide to dichloroacetyl chloride proceeds, the increase in the intensity of the color bodies tends to inhibit the passage of ultraviolet light rays through the reaction mass resulting in a substantial inhibition of the reaction rate resulting in slower overall reaction rates which are commercially unattractive. Upon completion of the reaction the color bodies must be removed prior to use of the dichloroacetyl chloride by oxidation of the colored species. The continued oxidative contact of the reaction mass results in further degradation of the dichloroacetyl chloride present in the reaction mass to such undesirable by-products as phosgene.

DESCRIPTION OF THE INVENTION

It has been discovered that the above-mentioned undesirable side effects of the rearrangement reaction of trichloroethylene oxide to dichloroacetyl chloride can be essentially eliminated by employing a completely new and novel catalyst for the rearrangement reaction. The catalyst can be selected from primary and secondary amides of the lower alkyls. By lower alkyls is meant those alkyls having from 1 to 6 carbon atoms. Preferably, dialkylformamide is used as the catalyst but most preferably, dimethylformamide is employed as the catalyst for this rearrangement reaction in a catalytically effective amount. The amount of catalyst employed can range from about 0.001 to about 1.0 volume percent of trichloroethylene in the reaction mixture and preferably from about 0.01 to 0.10 volume percent of the amide based on trichloroethylene.

In the present improved process for the manufacture of dichloroacetyl chloride by the photochemical oxidation of trichloroethylene to dichloroacetyl chloride and trichloroethylene oxide with continuous rearrangement of the trichloroethylene oxide to dichloroacetyl chloride, the reaction consists of reacting trichloroethylene with oxygen or air in the presence of light, a catalytic amount of free chlorine or bromine, and the above-mentioned amide catalyst in the liquid phase. The catalytic amount of free chlorine or bromine can be from about 0.1 mole to about 3.84 mole %, preferably from about 0.8 mole % to about 3.84 mole % of the oxygen added without effecting further chlorination of the trichloroethylene.

The amide catalyst for the rearrangement of the trichloroethylene oxide to dichloroacetyl chloride can be added in several aliquot portions at the beginning and distributed throughout the period of the liquid phase oxidative reaction of trichloroethylene to dichloroacetyl chloride and trichloroethylene oxide or it can be added continuously to the reaction mass during a batch operation or continuously added with the trichloroethylene feed to a continuous process reaction. By addition of the amide catalyst at the beginning of the reaction and continuously or periodically adding additional amounts of catalyst as the catalyst is consumed, the build-up of ethylene oxide in the system is virtually eliminated and the reaction proceeds smoothly and is easily controlled in terms of temperature and rate of reaction, with no build-up of colored by-products in the reaction mixture due to their continuous oxidation to non-colored by-products.

The reaction can be conducted at temperatures ranging from about 24° C to about 100° C, preferably from about 60° C to about 90° C, and most preferably from about 65° C to about 80° C.

The oxygen is preferably added in the form of $O_2$, but of course, could alternately be added in the form of straight air. A chlorine activating source such as ultraviolet light is preferred for the reaction. The ultraviolet light wave range preferred for this reaction is that sufficient to cause the disassociation of chlorine to create a free radical. Normally such ultraviolet lights are within the chlorine absorption band and sufficient to activate the chlorine molecule.

The product of this reaction remains essentially optically clear throughout the reaction so that significantly higher rates of reaction are obtained while achieving yields of approximately 85% to 90% based on trichloroethylene used.

In order to illustrate the merits of the present invention, the following examples are provided.

EXAMPLE 1

The reactions are conducted in a resin kettle approximately 4¾ inches in diameter and filled to a depth of about 13 inches with 2½ liters with trichloroethylene. The kettle was equipped with a fritted gas sparger, an agitator, a thermometer and a reflux condenser. Illumination was furnished by F15T8 B1 fluorescent lights. Emmision of these 15 watt lights peaks at approximately 3000A°. The oxidations were effected by bubbling $O_2$ containing 1 mole % of $Cl_2$ through the reaction mixture. The oxidations were begun at room temperature and after an hour or so, sufficient heat had been generated to require cooling.

Into the above reactor was charged 3624 g $CCl_2=CHCl$ (trichloroethylene). The major part of the oxidation took place at 70°–80° C. The oxidation was continued until dichloroacetyl chloride ($CHCl_2COCl$) constituted 90% of the material. The remainder was unreacted trichloroethylene. The recovered material weighed 3570 grams and contained 3213 grams DCAC and 357 grams trichloroethylene. Thus 3267 grams trichloroethylene were oxidized and should have yielded 3603 grams DCAC. The resultant yield based on consumed trichloroethylene was 89.2% at a 90% conversion rate. Dimethylformamide was added during the oxidation, at the beginning of the reaction and in equal portions during the entire conduct of the reaction, resulting in no TCEO build-up. A total of 8 ml of dimethylformamide were used.

EXAMPLE 2

This example was conducted in the manner of Example 1, except that 3631 grams of trichloroethylene were charged to the reactor and the major portion of the oxidation took place between 60°–65° C. 3631 grams of materials were recovered containing 23% trichloroethylene and 77% dichloroacetyl chloride. Thus, at this conversion, the yield was 90.7%. Initially 5 milliters of dimethylformamide was added to the reaction mixture and then when the oxidation had reached 44% of completion, approximately ⅓ ml more was added over an 1 hour period of time.

What is claimed is:

1. In a process for producing dichloroacetyl chloride comprising reacting trichloroethylene in the liquid phase with an oxygen containing gas in the presence of a catalytic amount of free chlorine or bromine and a chlorine activating source to form a mixture of dichloroacetyl chloride and trichloroethylene oxide, and then treating said mixture with a catalytically effective amount of an amine catalyst to cause rearrangement of the trichloroethylene oxide to dichloroacetyl chloride, the improvement comprising continuously contacting the reaction mixture of trichloroethylene and oxygen during the oxidation of the trichloroethylene with an amide catalyst selected from the group of primary alkyl amides and secondary alkyl amides, in which the alkyl groups contain from 1 to 6 carbon atoms to effect continuous rearrangement of trichloroethylene oxide formed to dichloroacetyl chloride.

2. The process of claim 1 wherein the catalyst is dialkyl formamide.

3. The process of claim 1 wherein the catalyst is dimethyl formamide.

4. The process of claim 1 wherein the amide catalyst added to the reaction mixture is from about 0.001 to 1.0 volume percent of trichloroethylene added to the reaction mixture.

5. The process of claim 1 wherein the amide catalyst added to the reaction mixture is from about 0.01 to about 0.10 volume percent of trichloroethylene added to the reaction mixture.

6. The process of claim 4 wherein the reaction temperature is from about 24° C to about 100° C.

7. The process of claim 5 wherein the reaction temperature is from about 60° C to about 90° C.

8. The process of claim 5 wherein the reaction temperature is from about 65° C to about 80° C.

* * * * *